United States Patent [19]

Paul et al.

[11] Patent Number: 4,962,231

[45] Date of Patent: Oct. 9, 1990

[54] PREPARATION OF D- OR L-ALANINE OR HIGH ENANTIOMERIC PURITY

[75] Inventors: Axel Paul, Mannheim; Peter Tonne, Neustadt; Eckhard Roske, Ludwigshafen; Hardo Siegel, Speyer, all of Fed. Rep. of Germany

[73] Assignee: BASF Aktiengesellschaft, Ludwigshafen, Fed. Rep. of Germany

[21] Appl. No.: 205,342

[22] Filed: Jun. 10, 1988

[30] Foreign Application Priority Data

Jun. 13, 1987 [DE] Fed. Rep. of Germany ....... 3719872

[51] Int. Cl.$^5$ .......................................... C07C 227/08
[52] U.S. Cl. .................................................... 562/575
[58] Field of Search ......................................... 562/575

[56] References Cited

U.S. PATENT DOCUMENTS

| | | | |
|---|---|---|---|
| 3,190,914 | 6/1964 | Williams | 562/575 |
| 3,475,489 | 10/1969 | de Graaf et al. | 562/575 |
| 3,642,887 | 2/1972 | Jackisch | 562/575 |
| 4,408,068 | 10/1983 | Koch | 560/226 |
| 4,705,752 | 11/1987 | Boesten et al. | 435/106 |

FOREIGN PATENT DOCUMENTS 0763329 9/1980 U.S.S.R. ............... 562/875

OTHER PUBLICATIONS

Gould, "Mechanism and Structure in Organic Chemistry", pp. 250–55, 262–69, (1963).
Morrison et al., "Organic Chemistry", pp. 731–2, (1966).
I. Ogata et al., Bull. Chem. Soc. Jpn. 54 (1981) 3605.
N. L. Wender, J. Amer. Chem. Soc. 71 (1949), 375.
Nature 166 (1950), 178–179, Brewster et al.
J. Organomet. Chem. 150, C14–C16, (1978).
Ogata et al., Chem. Abstract, vol. 95, No. 5, p. 881, 43612e, (Aug. 1981).
Ber. 51, pp. 1315–1322, (1918).
Ber. 40, pp. 489–493, (1907).

Primary Examiner—James H. Reamer
Attorney, Agent, or Firm—Keil & Weinkauf

[57] ABSTRACT

A pure D- or L-alanine enantiomer is prepared by reacting an optically active chloropropionic acid with ammonia in water or a water/alcohol mixture at from 50° to 110° C.

7 Claims, No Drawings

PREPARATION OF D- OR L-ALANINE OR HIGH ENANTIOMERIC PURITY

The present invention relates to a process for the preparation of D- or L-alanine of high enantiomeric purity, wherein an optically active chloropropionic acid having high enantiomeric purity is reacted with ammonia or an ammonia-donating compound in water or a water/ alcohol mixture at from 50 to 110° C.

The preparation of racemic D,L-alanine from halopropionic acids has been described in many publications. J. Ogata et al., Bull. Chem. Soc. Jpn. 54 (1981), 3605, state that D,L-chloropropionic acid can be converted into D,L-alanine by reaction with an excess of $NH_3$ in water at 70° C.

It is also known that, for example, β-alanine can be prepared from β-bromopropionic acid (N. L. Wender, J. Amer. Chem. Soc. 71 (1949), 375). In this procedure, the β-bromopropionic acid is reacted with not less than a stoichiometric amount of urotropine. The resulting quaternary ammonium salt is then cleaved with concentrated HCl to give β-alanine hydrochloride.

US-A 3 190 914 furthermore describes a process which is particularly suitable for the preparation of glycine from chloroacetic acid. In this procedure, not less than a stoichiometric amount, based on the chloroacetic acid, of urotropine and in addition an excess of $NH_3$ in water are used.

According to USSR Patent 763,329, D,L-alanine, inter alia, is obtained from D,L-chloropropionic acid by reaction with $NH_3/H_2O$ with the addition of melamine, urotropine or cyanuric acid (usually 15%, based on D,L-chloropropionic acid).

The two last-mentioned processes manage without acidic hydrolysis, and the amino acid is obtained directly.

This process which is known for the reaction of racemic chlorocarboxylic acids was apparently not considered capable of being extrapolated to optically active starting material without the danger of racemization, since all processes described for the preparation of D-alanine follow more complicated and more expensive routes.

These are, in addition to the preparation of D-alanine by fermentation and various methods for the resolution of racemic alanine by enzymatic means and crystallization, a large number of relatively expensive enantioselective syntheses for the preparation of D-alanine, which furthermore give products having unsatisfactory enantiomeric purity in some cases. Nature 166 (1950), 178–179 discloses, for example, the reaction of L-α-bromopropionic acid with $NaN_3$ followed by hydrogenation. Furthermore, the enantioselective hydrogenation of pyruvic acid or acetamidoacrylic acid under aminating conditions according to J. Organomet. Chem. 150 (1978), C14–C16 leads to D-alanine. According to GB-A 2 100 264, it is also possible to obtain D-alanine from the mesylate of L-lactates by reaction with benzylamine, hydrogenation and hydrolysis. Finally, the enantioselective enzymatic cleavage of D,L-alaninamide leads to D-alanine and L-alaninamide, according to NL-A 84/ 3093.

We have found a process for the preparation of D- or L-alanine of high enantiomeric purity, wherein an optically active chloropropionic acid of high enantiomeric purity is reacted with ammonia or an ammonia-donating compound in water or a water/alcohol mixture at from 50 to 110° C.

The reaction is equally suitable for the preparation of D-alanine from L-chloropropionic acid and of L-alanine from D-chloropropionic acid. In particular, the process is used for the preparation of D-alanine from L-propionic acid.

Advantageously, the total amount of the ammonia or the ammonia-donating reagent used is not less than twice the molar amount, based on the chloropropionic acid. As a rule, the ammonia is added in an amount such that a pH of from 6 to 9, preferably from 6.5 to 7.5, is maintained.

An example of a suitable ammonia-donating compound is urotropine. The urotropine can advantageously be used in an amount of, for example, from 10 to 100, preferably from 15 to 30, mol %, based on L-chloropropionic acid. However, larger amounts are also possible.

Examples of alcohols are low molecular weight, preferably water-soluble alcohols, eg. methanol, ethanol, isopropanol, n-propanol, n-butanol and isobutanol, and the volume ratio of water to alcohol can be from 60:40 to 100:0.

Instead of the free chloropropionic acid, it is also possible to start from the corresponding alkali metal or alkaline earth metal salts, although it is advisable partially or completely to liberate the free acid by reaction with hydrochloric acid, in order to prevent the formation of byproducts, such as 2,2'-iminodipropionic acid. It is of course also possible to use the ammonium salt of chloropropionic acid as a starting material. In this case, the minimum amount of ammonia required for chlorine substitution is the molar amount.

Specifically, the following general procedure is adopted for the reaction according to the invention: The L-chloropropionic acid is initially taken in the form of an aqueous salt-free or salt-containing, eg. NaCl-containing or $Na_2SO_4$-containing, solution. The amount of water is usually chosen so that a homogeneous solution is just obtained. However, it is also possible to use a larger amount of water. Instead of water, water/alcohol mixtures can also be used. A pH of about 6–7 is obtained by adding dilute ammonia solution, eg. 25% strength ammonia water, after which the desired amount of urotropine is added. The order in which the urotropine and ammonia solution are added can of course be changed. The reaction mixture is then heated to the reaction temperature of from 50 to 110° C., in particular from 50 to 90° C., preferably from 60 to 70° C., the pH of the solution being kept at from 6 to 9, in particular from 6.5 to 7.5, preferably from 6.8 to 7.2, by adding dilute ammonia solution. For 20 mol %, based on L-chloropropionic acid, of urotropine, the reaction time is about 4 hours. The reaction time can be reduced by using larger amounts of urotropine.

When the reaction is carried out in the absence of urotropine, it is possible, for example, to adopt the following procedure: the L-chloropropionic acid or its alkali metal or alkaline earth metal salt is dissolved in from 5 to 15, preferably 10, times the molar amount of ammonia water (eg. 25% strength), and the reaction mixture is stirred in a pressure-tight vessel under autogenous pressure at the reaction temperature. At 70° C., the reaction is complete after about 5 hours.

The reaction mixtures can be worked up in a conventional manner. For example, the inorganic salts in solution in the discharge reaction mixture can be reduced to the desired percentage concentration, the known electrodialysis processes being particularly suitable for this purpose. Any urotropine present in the reaction mixture can be eliminated, for example, by hydrolysis, by salt formation with organic acids or in particular mineral acids, or by reduction with formic acid. The D-alanine can advantageously be isolated by selective crystallization after the solution has been evaporated down.

The optically active chloropropionic acids used as starting materials are obtainable in industrial amounts from the corresponding optically active lactic acids prepared by an enzymatic method (in this context, see EP-A 00 56 981).

EXAMPLE 1

10.2 g (0.094 mole) of L-chloropropionic acid (96% ee) was stirred together with 150 g (2.2 moles) of 25% strength $NH_3$ solution for 5 hours at 70° C. in an autoclave. The discharged mixture was brought to pH 6.1 with concentrated HCl and salts were removed by electrodialy-sis. Subsequent crystallization by evaporating down the aqueous solution gave 5.8 g (0.065 mole) of pure D-alanine (70% yield, ee >98%).

EXAMPLE 2

108.5 g (1 mole) of L-chloropropionic acid (96% ee) were dissolved in 160 ml of water, 28 g (0.2 mole) of urotropine and 66.8 g (0.98 mole) of 25% strength aqueous $NH_3$ solution were added and the mixture was heated to 65° C. 67.5 g (1.0 mole) of 25% strength $NH_3$ solution were metered in at a rate such that the pH of the reaction mixture was always 6.9. The reaction time was about 4 hours. The discharged mixture was brought to pH 6.1 with HCl and 250 ml of water were added, so that a homogeneous solution was obtained. Salts were removed from this solution by electrodialysis, until the chloride content was 0.04%. Subsequent crystallization gave 65 g (0.73 mole) of D-alanine (73% yield, ee >98%).

EXAMPLE 3

96 g (1 mole) of 38% strength HCl were added to a solution of 130.5 g (1 mole) of Na L-chloropropionate (ee 96%), obtained by hydrolyzing an L-chloropropionate. 28 g (0.2 mole) of urotropine and 67.5 g (1 mole) of 25% strength aqueous $NH_3$ solution were added to the mixture, which was then heated to 65° C. and reacted further as described in Example 2. 64 g (0.72 mole) of D-alanine were obtained (72% yield, ee >98%).

We claim:

1. A process for the preparation of D—or L—alanine of high enantiomeric purity which comprises: reacting an optically active chloropropionic acid of high enantiomeric purity with ammonia or an ammonia-donating compound in water or a water/alcohol mixture at from 50 to 110° C. wherein the total amount of ammonia or ammonia-donating compound used is not less than 2 moles per mole of said chloropropionic acid and said ammonia or ammonia-donating compound is added in an amount such that a pH of 6 to 9 is maintained.

2. The process of claim 1, wherein the ammonia-donating compound used is urotropine.

3. The process of claim 1, wherein a mixture of ammonia and urotropine is used.

4. The process of claim 1, wherein the reaction is carried out at from 50 to 90° C. and at a pH of from 6.5 to 7.5.

5. The process of claim 1, wherein D-alanine is prepared from L-chloropropionic acid.

6. The process of claim 1, wherein L-alanine is prepared from D-chloropropionic acid.

7. The process of claim 1, wherein the reaction is carried out at from 60 to 70° C. and at a pH of from 6.8 to 7.2.

* * * * *